United States Patent
Ansmann et al.

(10) Patent No.: US 6,280,712 B1
(45) Date of Patent: Aug. 28, 2001

(54) SUN SCREEN AGENTS

(75) Inventors: Achim Ansmann, Erkrath; Helga Gondek, Duesseldorf; Rolf Kawa, Monheim; Holger Tesmann, Juechen, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/486,600

(22) PCT Filed: Aug. 20, 1998

(86) PCT No.: PCT/EP98/05293
§ 371 Date: May 24, 2000
§ 102(e) Date: May 24, 2000

(87) PCT Pub. No.: WO99/11235
PCT Pub. Date: Mar. 11, 1999

(30) Foreign Application Priority Data

Aug. 29, 1997 (DE) .............................. 197 37 737

(51) Int. Cl.$^7$ .............................. A61K 7/42; A61K 7/44; A61K 7/00
(52) U.S. Cl. .............................. 424/59; 424/60; 424/400; 424/401
(58) Field of Search .............................. 424/59, 60, 400, 424/401

(56) References Cited

U.S. PATENT DOCUMENTS

| | | |
|---|---|---|
| 4,395,370 | 7/1983 | Boden et al. . |
| 5,705,169 | 1/1998 | Stein et al. . |
| 5,730,960 | 3/1998 | Stein et al. . |

FOREIGN PATENT DOCUMENTS

| | | |
|---|---|---|
| 11 65 574 | 3/1964 | (DE) . |
| 20 24 051 | 5/1986 | (DE) . |
| 196 31 792 | 3/1997 | (DE) . |
| 196 32 043 | 2/1998 | (DE) . |
| 0 693 471 | 1/1996 | (EP) . |
| 0 694 521 | 1/1996 | (EP) . |
| 0 818 450 | 1/1998 | (EP) . |
| 962 919 | 7/1964 | (GB) . |
| 1 333 475 | 10/1973 | (GB) . |
| WO92/22282 | 12/1992 | (WO) . |
| WO97/47281 | 12/1997 | (WO) . |
| WO97/47282 | 12/1997 | (WO) . |

OTHER PUBLICATIONS

Ansmann, et al., Information Kosmetik, MYRITOL™ 331, No. III/97, Jan., 1997, Henkel KgaA, Duesseldorf, Germany.

P. Finkel, SÖFW–Journal, 122, (Aug., 1996), pp. 543–546 & 548.

Kosmetische Färbemittel, Farbstoffkommission der Deutschen Forschungsgemeinschaft, Verlag Chemie, Weinheim, (1984), pp. 81–106.

"Kosmetik–Entwicklung, Herstellung und Anwendung kosmetischer Mittel", Ed. W. Umbach, Georg Thieme Verlag Stuttgart, New York, (1988), pp. 124–125.

*Primary Examiner*—Shelley A. Dodson
(74) *Attorney, Agent, or Firm*—John E. Drach; Steven J. Trzaska

(57) ABSTRACT

A process for enhancing the effectiveness of a sunscreen lotion containing at least one ultraviolet filter involving solubilizing/dispersing the ultraviolet filter in a dialkyl/alkenyl carbonate.

10 Claims, No Drawings

SUN SCREEN AGENTS

BACKGROUND OF THE INVENTION

This invention relates to sun protection compositions containing dialkyl carbonates and UV filters and to the use of the dialkyl carbonates as solvents or dispersants for UV filters.

In the production of sun protection compositions, it is important inter alia to dissolve or disperse the insoluble UV filters so reliably that sedimentation is avoided, even in the event of prolonged storage. It is known from the customer information booklet "INFORMATION Kosmetik No. III/97 of Henkel KGaA (January 1997) that coconut fatty acid glycerides commercially available as Myritol 331 have good dissolving properties for crystalline UV filters and increase UV absorption by comparison with non-polar UV filters. Sun protection compositions containing these substances are also known, for example, from DE-A1 19631792 (Henkel). Besides the stability of the compositions, however, an equally important quality feature so far as the consumer is concerned is that the compositions should spread quickly and lastingly on the skin which requires the presence of a carefully balanced mixture of oil components from various spreading ranges. In the case of sun protection compositions, relatively high percentages of quick-spreading oils are required to support the rapid and uniform spreading of the sensorially heavy UV filters.

Accordingly, the complex problem addressed by the present invention was to provide oil components which would be high-spreading, which would have good dissolving or dispersing properties for UV filters and which, at the same time, would synergistically support UV absorption.

DESCRIPTION OF THE INVENTION

The present invention relates to sun protection compositions containing
(a) dialkyl carbonates and
(b) UV filters.

It has surprisingly been found that, in contrast to other high-spreading oils, for example dialkyl ethers or cyclomethicone, dialkyl carbonates, more particularly di-n-octyl carbonate and di-2-ethylhexyl carbonate have a distinctly higher dissolving power for UV filters and, in addition, synergistically enhance UV absorption. The expert is thus able to build up a spreading "cascade" of high- and medium-spreading oils which are capable of converting large amounts of UV filters into stable solutions or dispersions. In addition, the concentration in which the filters are used, as calculated for the required protection factor, can be reduced which, ultimately, leads to a reduction in the raw material costs for the same performance.

Dialkyl Carbonates

Formally, dialkyl carbonates are esters of carbonic acid and preferably correspond to formula (I):

$$R^1O\text{---}CO\text{---}OR^2 \tag{I}$$

in which $R^1$ and $R^2$ independently of one another represent linear or branched alkyl and/or alkenyl groups containing 1 to 22 carbon atoms, with the proviso that they contain in all at least 12, preferably 12 to 50 and more preferably 15 to 25 carbon atoms. The compounds are obtained by transesterifying dimethyl or diethyl carbonate, for example, with the corresponding fatty alcohols in known manner. Accordingly, the fatty carbonates may be symmetrical or non-symmetrical. However, carbonates in which $R^1$ and $R^2$ are the same and represent $C_{6-16}$ alkyl groups are preferably used. Transesterification products of dimethyl or diethyl carbonate with octanol, 2-ethylhexyl alcohol, decanol, cetyl alcohol, cetearyl alcohol, stearyl alcohol, isostearyl alcohol, oleyl alcohol, behenyl alcohol and/or erucyl alcohol in the form of their mono- and diesters or technical mixtures and Guerbet alcohols containing 8 to 24 carbon atoms are particularly preferred. From the performance point of view, it has proved to be effective to use di-n-octyl carbonate or di-2-ethylhexyl carbonate which have a Zeidler spreading value of 1600 mm$^2$/10 mins. The dialkyl carbonates may be used in quantities of 1 to 30% by weight, preferably 5 to 20% by weight and more preferably 8 to 10% by weight, based on the composition.

UV Filters

UV filters in the context of the invention are organic substances which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP-B1 0693471;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP-A1 0818450;

propane-1,3-diones such as, for example, 1-(4-tert.butylphenyl)-3-(4'-methoxyphenyl)-propane-1,3-dione;

ketotricyclo(5.2.1.0)decane derivatives as described in EP-B1 0694521.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3 dione. The UV-A and UV-B filters may of course also be used in the form of mixtures. Besides the soluble substances mentioned, insoluble pigments, i.e. finely dispersed metal oxides or salts, for example titanium dioxide, zinc oxide, iron oxide, aluminium oxide, cerium oxide, zirconium oxide, silicates (talcum), barium sulfate and zinc stearate, may also be used for this purpose. The particles should have a mean diameter of less than 100 nm, preferably between 5 and 50 nm and more preferably between 15 and 30 nm. They may be spherical in shape although ellipsoidal particles or other non-spherical particles may also be used. Other suitable UV filters can be found in P. Finkel's review in SOFW—Journal 122, 543 (1996).

Besides the two groups of sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D, L-camosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to $\mu$mole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Commercial Applications

Dialkyl carbonates and, in particular, di-n-octyl or di-2-ethylhexyl carbonate have excellent dissolving properties for UV filters, are high-spreading and synergistically enhance UV absorption. Accordingly, the present invention also relates to their use as solvents or dispersants for UV filters.

The sun protection compositions may contain mild surfactants, oil components, emulsifiers, superfatting agents, stabilizers, consistency factors, thickeners, biogenic agents, preservatives, hydrotropes, solubilizers, insect repellents, self-tanning agents, perfume oils, dyes and the like as further auxiliaries and additives. The solids content of the compositions is normally in the range from 20 to 60% by weight and preferably in the range from 30 to 45% by weight.

Typical examples of suitable mild, i.e. dermatologically compatible, surfactants, are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, ether carboxylic acids, alkyl oligoglucosides, fatty acid glucamides, alkyl amidobetaines and/or protein fatty acid condensates (preferably based on wheat proteins).

Suitable other oil components are, for example, Guerbet alcohols based on fatty alcohols containing 6 to 18 and preferably 8 to 10 carbon atoms, esters of linear $C_{6-22}$ fatty acids with $C_{6-22}$ fatty alcohols, esters o branched $C_{6-13}$ carboxylic acids with linear $C_{6-22}$ fatty alcohols, esters of linear $C_{6-22}$ fatty acids with branched alcohols, more particularly 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, vegetable oils, branched primary alcohols, substituted cyclohexanes, linear $C_{6-22}$ fatty alcohol carbonates, Guerbet carbonates, esters of benzoic acid with linear and/or branched $C_{6-22}$ alcohols (for example Finsolv® TN), dialkyl ethers, ring opening products of epoxidized fatty acid esters with polyols, silicone oils and/or aliphatic or naphthenic hydrocarbons.

Suitable emulsifiers are, for example, nonionic surfactants from at least one of the following groups:

(1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;

(2) $C_{12/18}$ fatty acid monoesters and diesters of adducts of 1 to 30 moles of ethylene oxide with glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) adducts of 15 to 60 moles of ethylene oxide with castor oil and/or hydrogenated castor oil;

(6) polyol esters and, in particular, polyglycerol esters such as, for example, polyglycerol polyricinoleate, polyglycerol poly-12-hydroxy-stearate or polyglycerol dimerate. Mixtures of compounds from several of these classes are also suitable;

(7) adducts of 2 to 15 moles of ethylene oxide with castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) trialkyl phosphates and mono-, di- and/or tri-PEG-alkylphosphates;

(10) wool wax alcohols;

(11) polysiloxane/polyalkyl polyether copolymers and corresponding derivatives;

(12) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol, and

(13) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

$C_{8/18}$ alkyl mono- and oligoglycosides, their production and their use as surfactants are known from the prior art. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. Besides ampholytic emulsifiers, quaternary emulsifiers may also be used, those of the esterquat type, especially methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols containing 12 to 22 and preferably 16 to 18 carbon atoms. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® from Goodrich or Synthalens® from Sigma), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Typical examples of fats are glycerides while suitable waxes are inter alia beeswax, carnauba wax, candelilla wax, montan wax, paraffin wax or microwaxes, optionally in combination with hydrophilic waxes, for example cetyl stearyl alcohol or partial glycerides. Metal salts of fatty acids such as, for example, magnesium, aluminium and/or zinc stearate may be used as stabilizers. In the context of the invention, biogenic agents are, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes. Pigments with sun protection properties are fine-particle metal oxides, for example titanium dioxide or zinc stearate. Montmorillonites, clay minerals, Pemulen and alkyl-modified Carbopol types (Goodrich) may be used as swelling agents for aqueous phases.

In addition, hydrotropes, for example ethanol, isopropyl alcohol or polyols, may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine.

Suitable preservatives are, for example, phenoxyethanol, formaldehyde solution, parabens, pentanediol or sorbic acid. Suitable insect repellents are N,N-diethyl-m-toluamide, 1,2-pentanediol or Insect Repellent 3535. A suitable self-tanning agent is dihydroxyacetone Suitable perfume oils are the extracts of blossoms (lavender, rose, jasmine, neroli), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example musk, civet and beaver, may also be used. Suitable synthetic or semisynthetic perfume oils are Ambroxan, eugenol, isoeugenol, citronellal, hydroxycitronellal, geraniol, citronellol, geranyl acetate, citral, ionone and methylionone.

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be produced by standard hot or cold processes and are preferably produced by the phase inversion temperature method.

EXAMPLES

Table 1 shows the performance properties of dialkyl carbonates compared with other high-spreading oils.

TABLE 1

| Properties of high-spreading oils | | | | |
|---|---|---|---|---|
| Oil/performance | D-n-octyl carbonate | Di-2-ethyl-hexyl carbonate | Dica-prylyl ether | Cyclomethicone |
| Zeidler spreading value [mm$^2$]/10 mins. | 1600 | 1600 | 1600 | >1600 (volatile) |
| Increase in absorption* [%]; [paraffin oil - 100%] | +20 | +18 | +5 | +17 |

TABLE 1-continued

| Properties of high-spreading oils | | | | |
|---|---|---|---|---|
| Oil/performance | D-n-octyl carbonate | Di-2-ethyl-hexyl carbonate | Dica-prylyl ether | Cyclomethicone |
| Solubility [% by weight] | | | | |
| Benzophenone-3 | 40 | 38 | 5 | 5 |
| Methylbenzylidene camphor | 20 | 18 | 5 | 1 |

*Conditions: 5 ppm octyl methoxy cinnamate, UV spectrometer, 1 cm cell 308 nm

In Table 2 below, formulation examples 1 to 7 correspond to the invention while Examples C1 and C2 are intended for comparison. The stability of the formulations was evaluated after storage for 4 weeks at 40° C.; (+)=stable, (−)= sedimentation.

TABLE 2

| Composition | Formulation Examples | | | | | | | | |
|---|---|---|---|---|---|---|---|---|---|
| | 1 | 2 | 3 | 4 | 5 | 6 | 7 | C1 | C2 |
| Cetearylglucoside (and) Cetearyl Alcohol | 4.2 | 5 | — | — | — | — | — | — | — |
| Lauryl Glucoside (and) Polyglyceryl-2 Dipolyhydroxystearate | — | — | 4 | — | — | — | — | — | — |
| Sodium Stearate | — | — | — | 3 | — | — | — | — | — |
| Ceteareth-20 | — | — | — | 1 | — | — | — | — | — |
| Cetyl Dimethicone Copolyol | — | — | — | — | 4 | — | — | — | — |
| Polyglyceryl-3 dimerate | — | — | — | — | — | 4 | — | — | — |
| Polyglyceryl-3 Diisostearate | — | — | — | — | 1 | 1 | 1 | 1 | — |
| Polyglyceryl-2 Dipolyhydroxystearate | — | — | — | — | — | — | — | 3 | 3 |
| Hydrogenated Palm Glycerides | 2 | — | 5 | 6 | — | — | — | — | — |
| Zinc Stearate | — | — | — | — | 1 | 1 | 1 | 1 | 1 |
| D-n-octylcarbonate | 8 | — | 8 | 8 | 8 | 8 | 8 | — | — |
| Di-2-ethylhexylcarbonate | — | 8 | — | — | — | — | — | — | — |
| Dicaprylyl Ether | — | — | — | — | — | — | — | 8 | 14 |
| Coco Glycerides | 6 | — | 6 | 6 | 6 | — | 6 | 6 | — |
| Octyl Methoxycinnamate | 5 | 5 | 5 | 5 | — | 5 | 5 | 5 | — |
| 4-Methylbenzylidene Camphor | 3 | 3 | — | 3 | 3 | 3 | 3 | 3 | 3 |
| Benzophenone-3 | 4 | 4 | 4 | 4 | 4 | 4 | — | 4 | 4 |
| Titanium Dioxide | 1 | 1 | — | 1 | 1 | 1 | 1 | — | 1 |
| Zinc Oxide | 1 | 1 | 1 | — | 1 | 1 | — | 1 | 1 |
| Octyl Triazone | 1 | 1 | 1 | 1 | 1 | 1 | 1 | 1 | — |
| Glycerin (86% by weight) | 5 | 5 | 5 | 5 | 5 | 5 | 5 | 5 | 5 |
| Water | to 100 | | | | | | | | |
| Stability after 4 w (40° C.) | + | + | + | + | + | + | + | − | − |

TABLE 3

Further Formulation Examples*

| Composition | 8 | 9 | 10 | 11 | 12 | 13 | 14 | 15 | 16 | 17 | 18 | 19 |
|---|---|---|---|---|---|---|---|---|---|---|---|---|
| Polyglyceryl-2-Dipolyhydroxystearate | 2 | 3 | — | 5 | — | — | — | — | — | — | — | — |
| Polyglyceryl-3-Diisostearate | 4 | 1 | — | — | — | — | — | — | — | — | — | — |
| Cetyl Dimethicone Copolyol | — | — | 3 | — | — | — | — | — | — | — | — | — |
| Cetearyl Glucoside (and) Cetearyl Alcohol | — | — | — | — | 4 | — | — | — | — | 4 | — | — |
| Sodium Cetylphosphate | — | — | — | — | — | 0.5 | — | — | — | — | — | 1 |
| Ceteareth 20 | — | — | — | — | — | — | — | 2 | — | — | — | — |
| Polyglyceryl-3 Methylglucoside Distearate | — | — | — | — | — | — | 4 | — | — | — | 3 | — |
| Polyglyceryl-2 Dihydroxystearate (and) Lauryl Glucoside (and) Glycerin | — | — | — | — | — | 3 | — | — | 2.7 | 2.5 | — | — |
| Beeswax | 3 | 2 | 5 | 2 | — | — | — | — | — | — | — | — |
| Glyceryl Stearate | — | — | — | — | — | 2 | 4 | — | — | — | 6 | 4 |
| Myristyl Alcohol | — | — | — | — | — | — | — | — | 2.5 | — | — | — |
| Cetearyl Alcohol | — | — | 2 | — | 2 | 4 | 2 | 4 | 1 | 4 | 2 | 1 |
| PVP/Hexadecene Copolymer | — | — | — | — | — | 3 | — | — | — | — | — | 2 |
| Cocoglycerides | 5 | — | 10 | — | 8 | 6 | 6 | — | — | 5 | 10 | 5 |
| $C_{12/15}$ Alkyl Benzoate | — | 6 | — | 2 | — | — | 3 | — | — | — | — | 2 |
| Dicaprylyl Carbonate | 5 | — | 6 | 8 | — | 5 | — | 3 | 5 | 4 | 8 | 6 |
| Dioctyl Carbonate | — | 4 | — | — | 6 | — | 4 | 4 | — | — | — | — |
| Oleyl Erucate | 2 | — | 3 | 5 | 6 | 3 | 3 | — | — | 5 | 2 | 4 |
| Dicaprylyl Ether | 3 | — | — | — | — | 1 | — | — | — | — | — | — |
| Mineral Oil | — | 4 | — | 4 | — | 2 | — | 10 | — | — | — | — |
| Hexyldecanol (and) Hexyldecyl Laurate | — | 7 | 3 | 7 | 4 | — | — | — | 17 | 1 | — | — |
| Panthenol | 1 | 1 | 1 | 1 | 1 | 1 | 1 | 1 | 1 | 1 | 1 | 1 |
| Bisabolol | 0.2 | 0.2 | 0.2 | 0.2 | 0.2 | 0.2 | 0.2 | 0.2 | 0.2 | 0.2 | 0.2 | 0.2 |
| Tocopherol/Tocopherol Acetate | 1 | 2 | 2 | 4 | 2 | 3 | 3 | 5 | 1 | 1 | 3 | 4 |
| Phenylbenzimidazole Sulfonic Acid | 3 | — | — | 3 | — | — | 2 | — | — | 2 | — | — |
| Octocrylene | — | 4 | — | — | — | 4 | 5 | — | — | — | — | 10 |
| Benzophenone-3 | 1.5 | — | — | 2 | 1.5 | — | — | — | 1 | 2 | 1 | — |
| 4-Methylbenzylidene Camphor | — | 2 | — | — | — | — | 2 | — | — | 2 | 2 | — |
| Isoamyl p-Methoxycinnamate | 5 | — | 4 | — | 2 | — | 4 | 10 | 4 | — | 3 | — |
| Octyl Methoxycinnamate | 5 | — | 4 | 3 | 2 | 3 | 4 | — | 4 | 10 | 3 | — |
| Octyl Triazone | 2 | 3 | 1 | 1 | 1 | 1 | 2 | — | 2 | 1 | 1 | 3 |
| Butyl Methoxydibenzoylmethane | — | — | 2 | — | — | 2 | — | 3 | — | — | — | 2 |
| Zinc Oxide | — | 6 | 6 | — | 4 | — | — | — | 5 | — | — | 5 |
| Titanium Dioxide | — | 2 | 2 | — | — | — | — | 5 | 5 | — | 5 | — |
| Magnesium Aluminium Silicates | — | — | — | — | — | — | — | — | 1 | — | 1 | — |
| Xanthan Gum | — | — | — | — | — | — | — | — | 0.5 | — | 0.5 | — |
| Carbomer | — | — | — | — | — | 0.5 | 0.2 | — | — | 0.5 | — | 0.2 |
| Glycerin | 5 | 5 | 5 | 5 | 5 | 5 | 5 | 5 | 5 | 5 | 5 | 5 |
| Water, preservative | | | | | | to 100 | | | | | | |

*8 = w/o sun protection cream, 9–11 = w/o sun protection lotions, 12, 15, 16, 19 = o/w sun protection creams, 13, 14, 17, 18 = o/w sun protection creams

What is claimed is:

1. A process for enhancing the effectiveness of a sunscreen lotion containing at least one ultraviolet filter comprising solubilizing/dispersing the ultraviolet filter in a dialkyl/alkenyl carbonate.

2. The process of claim 1 wherein the dialkyl/alkenyl carbonate corresponds to formula I:

$$R^1O\text{—}CO\text{—}OR^2 \qquad (I)$$

wherein $R^1$ and $R^2$, independently of one another, represent linear or branched alkyl and/or alkenyl groups containing from 1 to 22 carbon atoms, with the proviso that the total number of carbon atoms is at least 12.

3. The process of claim 2 wherein the dialkyl/alkenyl carbonate is selected from the group consisting of di-n-octyl carbonate, di-2-ethylhexyl carbonate, and mixtures thereof.

4. The process of claim 1 wherein the ultraviolet filter is selected from the group consisting of 3-benzylidene camphor and its derivatives, 4-aminobenzoic acid derivatives, cinnamic acid esters, salicylic acid esters, benzophenone derivatives, benzalmalonic acids, triazine derivatives, propane-1,3-diones, 2-phenylbenzimidazole-5-sulfonic acids, benzophenone sulfonic acids, benzoyl methane derivatives, finely dispersed metal oxides, Superoxid-Dismutase, tocopherols, ascorbic acid, and mixtures thereof.

5. A process for making a sunscreen composition comprising:
   (a) providing at least one ultraviolet filter;
   (b) providing a dialkyl/alkenyl carbonate dispersant/solubilizer; and
   (c) mixing the ultraviolet filter and the dialkyl/alkenyl carbonate.

6. The process of claim 5 wherein the dialkyl/alkenyl carbonate corresponds to formula I:

$$R^1 O\text{—}CO\text{—}OR^2 \qquad (I)$$

wherein $R^1$ and $R^2$, independently of one another, represent linear or branched alkyl and/or alkenyl groups containing from 1 to 22 carbon atoms, with the proviso that the total number of carbon atoms is at least 12.

7. The process of claim 6 wherein the dialkyl/alkenyl carbonate is selected from the group consisting of di-n-octyl carbonate, di-2-ethylhexyl carbonate, and mixtures thereof.

8. The process of claim 5 wherein the ultraviolet filter is selected from the group consisting of 3-benzylidene camphor and its derivatives, 4-aminobenzoic acid derivatives, cinnamic acid esters, salicylic acid esters, benzophenone derivatives, benzalmalonic acids, triazine derivatives, propane-1,3-diones, 2-phenylbenzimidazole-5-sulfonic acids, benzophenone sulfonic acids, benzoyl methane derivatives, finely dispersed metal oxides, Superoxid-Dismutase, tocopherols, ascorbic acid, and mixtures thereof.

9. The process of claim 5 wherein the ultraviolet filters are present in the sunscreen composition in an amount of from 0.1 to 5% by weight, based on the weight of the composition.

10. The process of claim 5 wherein the dialkyllalkenyl carbonate is present in the composition in an amount of from 1 to 30% by weight, based on the weight of the composition.

* * * * *